United States Patent
Taoka et al.

(10) Patent No.: US 6,331,641 B1
(45) Date of Patent: Dec. 18, 2001

(54) PROCESS FOR PRODUCING SIMVASTATIN

(75) Inventors: Naoaki Taoka, Kobe; Kenji Inoue, Kakogawa, both of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/601,794

(22) PCT Filed: Dec. 10, 1999

(86) PCT No.: PCT/JP99/06929

§ 371 Date: Sep. 28, 2000

§ 102(e) Date: Sep. 28, 2000

(87) PCT Pub. No.: WO00/34264

PCT Pub. Date: Jun. 15, 2000

(30) Foreign Application Priority Data

Dec. 10, 1998 (JP) .................................................. 10-351865

(51) Int. Cl.$^7$ ..................... C07D 309/30; C07D 319/06; C07C 69/34
(52) U.S. Cl. ........................... 549/292; 549/375; 560/194
(58) Field of Search ............................ 560/194; 549/292, 549/375

(56) References Cited

U.S. PATENT DOCUMENTS 4,444,784 * 4/1984 Hoffmann et al. .................... 424/279
5,393,893 * 2/1995 Kubela et al. ........................ 549/292
6,100,407 * 8/2000 Van Dalen et al. .................. 549/196

FOREIGN PATENT DOCUMENTS

WO 98/12188 * 3/1998 (WO) .

OTHER PUBLICATIONS

Stretiwieser, A. et al "Introduction to Organic Chemistry" Macmillan Publishing Co., New York, pp. 473–476, 1976.*

* cited by examiner

Primary Examiner—Gary Geist
Assistant Examiner—Leigh C. Maier
(74) Attorney, Agent, or Firm—Connolly Bove Lodge & Hutz

(57) ABSTRACT

This invention provides an easy and efficient process for producing a simvastatin of great use as an HMG-CoA reductase inhibitor, which comprises deacylation of lovastatin with an inorganic base and a secondary or tertiary alcohol and subjecting the resulting diol lactone to selective protection with a ketal or acetal protective group, acylation and deprotection-lactonization to give simvastatin.

17 Claims, No Drawings

PROCESS FOR PRODUCING SIMVASTATIN

TECHNICAL FIELD

The present invention relates to a process for producing a simvastatin which comprises deacylating lovastatin with an inorganic base and a secondary or tertiary alcohol to give a diol lactone and subjecting it serially to selective protection with a ketal or acetal protective group, acylation and deprotection-lactonization. Simvastatin is known to be a compound of use as an HMG-CoA reductase inhibitor.

BACKGROUND ART

The production technology for simvastatin, heretofore known, includes (1) the process comprising hydrolysis of lovastatin with lithium hydroxide, lactonization to give a diol lactone, selective silylation with TBDS, acylation and desilylation (U.S. Pat. No. 4,444,784), (2) the process in which lovastatin potassium salt is directly methylated (U.S. Pat. No. 4,582,915), and (3) the process in which lovastatin monoalkylamide is directly methylated (U.S. Pat. No. 4,820,850), among others.

The above process (1) requires a high temperature and a long time for the hydrolysis reaction so that both yield and productivity are low. Moreover, the selective silylation and subsequent steps are not satisfactory enough in reaction selectivity so that the total yield is not as high as desired. In the process (2), the starting lovastatin partially remains unreacted so that a complicated procedure is required for purification. In the process (3), the reaction must be conducted at an extremely low temperature. Thus, all of the processes have much to be improved for commercial-scale production.

SUMMARY OF THE INVENTION

The inventors of the present invention explored for a technology by which simvastatin may be produced with high efficiency without using costly reagents and under comparatively mild conditions and arrived at a novel process which comprises deacylation of lovastatin with an inorganic base and a secondary or tertiary alcohol and subjecting the resulting diol lactone to selective protection with a ketal or acetal protective group, acylation and deprotection-lactonization to give simvastatin. The present invention has been accordingly developed.

The present invention, therefore, relates to a process for producing a simvastatin of the formula;

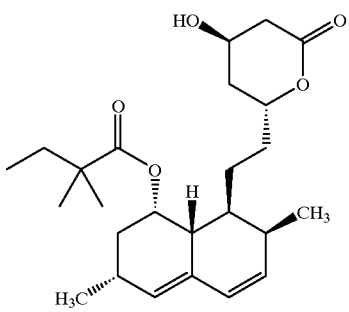

(6)

which comprises treating lovastatin of the formula (1) with an inorganic base and a secondary or tertiary alcohol to give a triol acid of the formula (2);

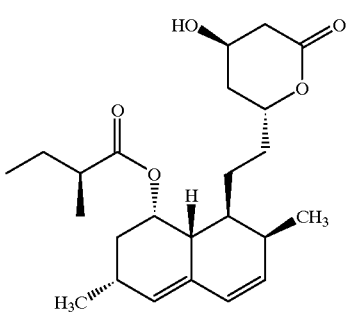

(1)

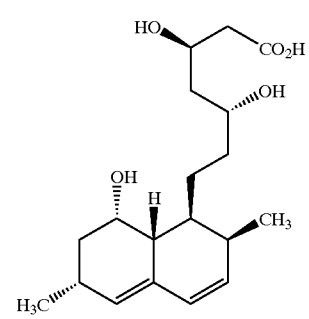

(2)

serially acidifying and lactonizing the triol acid (2) to give a diol lactone of the formula (3);

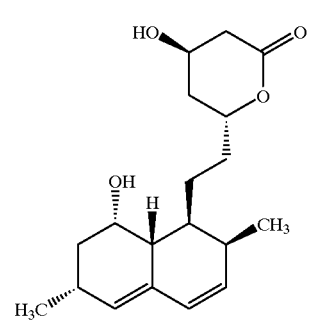

(3)

treating the triol acid (2) or diol lactone (3) with an acid and a compound of the formula $(RO)_2CR^1R^2$;

wherein R represents a lower alkyl group of 1 to 8 carbon atoms;

R$^1$ and R$^2$ may be the same or different and each represents hydrogen, a lower alkyl group of 1 to 8 carbon atoms, or an aryl or aralkyl group which may have a substituted group, or R$^1$ and R$^2$ may be coupled at the free ends to form a ring, to give a triol acid derivative of the formula (4);

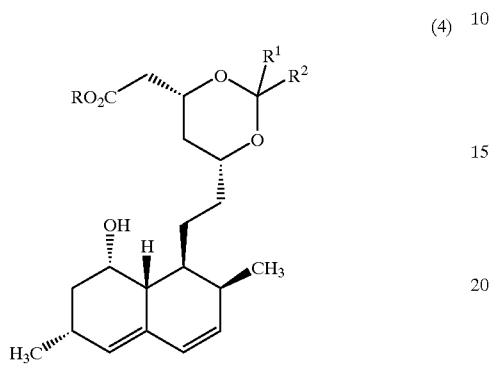

(4)

wherein R, R$^1$ and R$^2$ are respectively as defined above, treating the triol acid derivative (4) with 2,2-dimethylbutyryl chloride to give a simvastatin derivative of the formula (5);

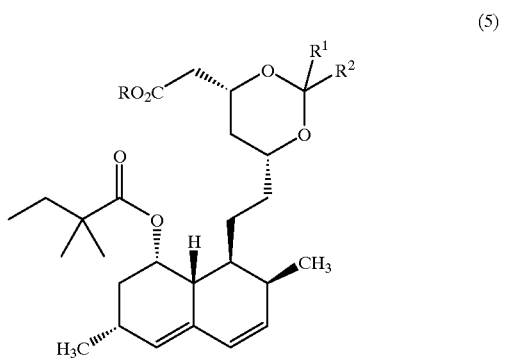

(5)

wherein R, R$^1$ and R$^2$ are respectively as defined above;

and treating the simvastatin derivative (5) with a protic solvent and an acid to give simvastatin (6).

The present invention further relates to a process for producing a diol lactone (3)

which comprises treating lovastatin (1) with an inorganic base and a secondary or tertiary alcohol to give a triol acid (2), serially acidifying and lactonizing the triol acid (2) to give a diol lactone (3).

The present invention further relates to a process for producing a triol acid derivative (4)

which comprises treating a triol acid (2) or a diol lactone (3) with an acid and a compound of the formula (RO)$_2$CR$^1$R$^2$; wherein R, R$^1$ and R$^2$ are respectively as defined above, to give a triol acid derivative (4).

The present invention further relates to a process for producing a simvastatin derivative (5)

which comprises treating a triol acid derivative (4) with 2,2-dimethylbutyryl chloride to give a simvastatin derivative The present invention further relates to a process for producing a simvastatin which comprises treating a simvastatin derivative (5) with a protic solvent and an acid to give simvastatin (6).

Lastly, the present invention relates to a triol acid derivative (4) and a simvastatin derivative (5).

The present invention is now described in detail.

DETAILED DESCRIPTION OF THE INVENTION

Lovastatin of the above formula (1), the starting compound of the invention, can be produced by a fermentation process employing a strain of microorganism belonging to the genus Aspergillus (U.S. Pat. No. 4,444,784).

The novel process of the present invention comprises deacylating lovastatin (1) with an inorganic base and a secondary or tertiary alcohol and subjecting the deacylated compound to lactonization to give a diol lactone (3), selective protection with a ketal- or acetal protective group, acylation, and deprotection-lactonization to give simvastatin of the formula (6) with high efficiency.

The process of the present invention is carried out as follows.

First, lovastatin (1) is treated with an inorganic base and a secondary or tertiary alcohol to give a triol acid (2). More particularly, lovastatin (1) is reacted with an inorganic base in the presence of a secondary or tertiary alcohol solvent in an inert atmosphere such as nitrogen gas to give a triol acid (2). The reaction temperature is 60 to 100° C. and the reaction time is 1 to 60 hours.

The secondary or tertiary alcohol mentioned above is preferably a secondary or tertiary alcohol the hydrocarbon moiety of which is an alkyl group containing 3 to 8 carbon atoms. Said alcohol is not particularly restricted but includes secondary alcohols such as isopropyl alcohol, sec-butyl alcohol and cyclohexanol and tertiary alcohols such as t-butyl alcohol. The preferred is isopropyl alcohol or t-butyl alcohol.

The inorganic base mentioned above is not particularly restricted but includes alkali metal hydroxides such as lithium hydroxide, sodium hydroxide, potassium hydroxide, etc.; and alkali metal alkoxides such as potassium t-butoxide, sodium isopropoxide, etc. The more preferred is potassium hydroxide. Usually, the inorganic base is used in a proportion of 1 to 10 molar equivalents to lovastatin (1).

Then, the triol acid (2) is acidified and lactonized to give a diol lactone (3). More particularly, the reaction mixture obtainable by the above treatment is concentrated under reduced pressure and the residue is acidified with an inorganic acid such as hydrochloric acid and sulfuric acid and extracted with an organic solvent. The extract is concentrated under reduced pressure to give an acidified triol acid (2). This acidified triol acid (2) is lactonized by heating in an organic solvent under reflux and the reaction product is caused to crystallize out from an organic solvent. The system is filtered and dried to give the diol lactone (3). Usually, the triol acid (2) is preferably not isolated but subjected to lactonization reaction in the form of a concentrate of the acidified reaction mixture.

The organic solvent for refluxing is not particularly restricted but includes toluene, hexane, ethyl acetate and isopropyl acetate, among others. The organic solvent for crystallization is not restricted, either but includes toluene, hexane, ethyl acetate and isopropyl acetate, among others.

Then, the triol acid (2) or diol lactone (3) is treated with an acid and a ketal or acetal in an organic solvent to give a triol acid derivative (4). The reaction temperature is 20 to 60° C. and the reaction time is 1 to 10 hours.

The formula $(RO)_2CR^1R^2$ for said ketal or acetal means a dialkoxy ketal or acetal. In the formula, R represents a lower alkyl group of 1 to 8 carbon atoms, such as methyl, ethyl, propyl, isopropyl, butyl, t-butyl, etc., and is preferably methyl. $R^1$ and $R^2$ may be the same or different and each represents hydrogen; a lower alkyl group of 1 to 8 carbon atoms, e.g. methyl, ethyl, propyl, isopropyl, butyl, t-butyl, etc.; an aryl group which may have a substituted group, such as phenyl, p-chlorophenyl, etc.; or an aralkyl group such as benzyl, p-chlorobenzyl, etc., or $R^1$ and $R^2$ may be coupled at free ends to form a ring. Preferably, both $R^1$ and $R^2$ respectively represent a methyl group. The ketal or acetal should be used theoretically in an equimolar proportion relative to the diol lactone (3) but actually is used in a proportion of 1 to 10 molar equivalents.

The acid mentioned above may for example be p-toluenesulfonic acid, methanesulfonic acid, camphorsulfonic acid, trifluoroacetic acid, hydrochloric acid or sulfuric acid, and acts as an acid catalyst. The amount of use of the acid is 0.01 to 1 molar equivalents relative to the diol lactone (3).

The organic solvent mentioned above should be a solvent which does not adversely affect the reaction but otherwise is not particularly restricted, but includes, for example, methylene chloride, acetone, toluene, hexane, ethyl acetate, methyl t-butyl ether, etc.

After the reaction, typically the reaction mixture is neutralized with a base, such as pyridine, and concentrated under reduced pressure, whereby the triol acid derivative (4) is obtained.

This triol acid derivative (4) is further reacted with 2,2-dimethylbutyryl chloride in the presence of an organic base and a tertiary amine to give the simvastatin derivative (5). The reaction temperature is 40 to 120° C. and the reaction time is 1 to 100 hours.

The organic base mentioned above is not particularly restricted but includes pyridine, 2-picoline, 3-picoline and 4-picoline, among others. The tertiary amine mentioned above is not particularly restricted, but includes 4-dimethylaminopyridine, 4-pyrrolidinopyridine and so on. These substances are used in the amounts of 10 to 60 moles and 0.01 to 1 mole, respectively, based on the triol acid derivative (4).

The reaction mixture thus obtained is concentrated under reduced pressure, added with an organic solvent such as ethyl acetate, washed with an acid, and finally concentrated under reduced pressure to give the simvastatin derivative (5).

Lastly, this simvastatin derivative (5) is treated with an acid catalyst and a protic solvent, preferably a small amount of water, in an organic solvent, whereby the same is converted to simvastatin (6). The reaction temperature is 20 to 60° C. and the reaction time is 1 to 10 hours.

The acid catalyst mentioned above is not particularly restricted but includes hydrochloric acid, sulfuric acid, methanesulfonic acid, camphorsulfonic acid and trifluoroacetic acid, among others. The acid catalyst is used in a proportion of 0.01 to 1 moles per mole of the simvastatin derivative (5).

The amount of water to be used is 1 to 100% of the organic solvent on a volume-volume basis.

The organic solvent mentioned above is not particularly restricted but includes acetonitrile, THF, methanol and so on.

The protic solvent mentioned above is not particularly restricted, either. Thus, not only water but also methanol, ethanol, n-propanol, i-propanol, etc. can be mentioned.

The reaction mixture thus obtained is concentrated under reduced pressure and the residue is crystallized from an organic solvent, such as cyclohexane, filtered, and dried to give simvastatin (6).

BEST MODE FOR CARRYING OUT THE INVENTION

The following examples illustrate the present invention in further detail and should by no means be construed as defining the scope of the invention.

In the following examples (Examples 7, 8 and 9), the triol acid (2) and/or the diol lactone (3) was determined qualitatively and quantitatively by high performance liquid chromatography under the following conditions (parameter setting A).

Parameter Setting A
Instrument: LC-10A, Shimadzu Corporation
Column: ODS column, Nakalai-Tesque, Cosmosil 5C18-AR-300
Eluent: acetonitrile/0.1% phosphoric acid (aq.)=100/50 (v/v)
Flow rate: 1.5 ml/min.
Detection: 238 nm (UV detector)
Temperature: 45° C.

The compounds of the formulas (3), (4), (5), and (6) derived from the triol acid were quantitated by high performance liquid chromatography under the following conditions (parameter setting B).

Parameter setting B
Instrument: LC-10A, Shimadzu Corporation
Column: ODS column, Nakalai-Tesque, Cosmosil 5C18-AR-300
Eluent: acetonitrile/0.1% phosphoric acid (aq.)=150/50 (v/v)
Flow rate: 1.0 ml/min.
Detection: 238 nm (UV detector)
Temperature: 45° C.

EXAMPLE 1

Process for Producing the Diol Lactone (compound of the formula (3))

To a solution of KOH (7.92 g) in 300 ml of t-butyl alcohol was added 8.09 g (20 mmol) of lovastatin, and the mixture was stirred under argon gas at room temperature for 30 minutes. Then, the temperature was raised and the mixture was refluxed with stirring for 4 hours. This reaction mixture was concentrated under reduced pressure, added with water, acidified with phosphoric acid (pH=3.5), and extracted with ethyl acetate. The extract was concentrated under reduced pressure to give a brown-colored oil. This brown-colored oil was dissolved in 200 ml of isopropyl acetate, and after addition of 65 µl (1 mmol) of methanesulfonic acid, the solution was concentrated to about ⅕ volume under reduced pressure. The residue was washed with saturated aqueous solution of sodium hydrogencarbonate, cooled to −20° C., and stirred. The resulting slurry was filtered and dried in vacuo to give white crystals. This product was identified to be the title compound.

EXAMPLE 2

Process for Producing 2,2-dimethyl-6 (R)-(2-(8-(S)-hydroxy-2(S),6(R)-dimethyl-1,2,6,7,8,8a(R)-hexahydronaphthyl-1(S))ethyl)-4(R)-(methyloxycarbonyl)methyl-1,3-dioxane (compound of the formula (4))

To a solution of the diol lactone (1.62 g, 5 mmol) in 25 ml of methylene chloride were added 3,69 ml (30 mmol) of 2, 2-dimethoxypropane and 48 mg (0.25 mmol) of p-toluenesulfonic acid, and the mixture was stirred under argon gas at room temperature for 1 hour. This reaction mixture was neutralized with pyridine and concentrated under reduced pressure, and the concentrate was purified by silica gel column chromatography to give a clear oil. This product was identified to be the title compound.

NMR(CDCl$_3$, 400 MHz) δ: 0.89 (d, 3H), 1.1–1.9 (m, 16H), 1.2 (d, 3H), 2.2–2.6 (m, 5H), 3.65 (s, 3H), 3.85 (m, 1H), 4.2 (m, 1H), 4.3 (m, 1H), 5.5 (bt, 1H), 5.78 (dd, 1H), 6.0 (d, 1H).

EXAMPLE 3

Process for Producing 2,2-dimethyl-6(R)-(2-(8(S)-(2,2-dimethylbutyryloxy)-2(S),6(R)-dimethyl-1,2,6,7,8,8a(R)-hexahydronaphthyl-1(S))ethyl)-4(R)-(methyloxycarbonyl)methyl-1,3-dioxane (compound of the formula (5))

To a solution of 2,2-dimethyl-6(R)-(2-(8-(S)-hydroxy-2(S),6(R)-dimethyl-1,2,6,7,8,8a(R)-hexahydronaphthyl-1(S))ethyl)-4(R)-(methyloxycarbonyl)methyl-1,3-dioxane (1.96 g, 5 mmol) in 16.2 ml (40 mmol) of pyridine were added 122 mg (1 mmol) of 4-dimethylaminopyridine and 2.69 g (20 mmol) of 2,2-dimethylbutyryl chloride, and the mixture was stirred at 100° C. for 6 hours. This reaction mixture was concentrated under reduced pressure and added with ethyl acetate. The organic layer was washed with 10% aqueous solution of citric acid and concentrated under reduced pressure. The residue was purified by silica gel column chromatography to give a clear oil. This product was identified to be the title compound.

NMR (CDCl$_3$, 400 MHz) δ: 0.88 (t, 3H), 0.89 (d, 3H), 1.08 (d, 3H), 1.11 (s, 3H), 1.12 (s, 3H), 1.2–1.7 (m, 11H), 1.35 (s, 3H), 1.45 (s, 3H), 1.88–2.6 (m, 5H), 3.65 (s, 3H), 3.7 (m, 1H), 4.3 (m, 1H), 5.3 (m, 1H), 5.5 (bt, 1H), 5.78 (dd, 1H), 6.0 (d, 1H).

EXAMPLE 4

Process for Producing Simyastatin (compound of the formula (6))

To a solution of 2,2-dimethyl-6(R)-(2-(8(S)-( 2,2)-dimethylbutyryloxy)-2(S),6(R)-dimethyl-1,2,6,7,8,8a(R)-hexahydronaphthyl-1(S))ethyl)-4(R)-(methyloxycarbonyl)methyl-1,3-dioxane (2.45 g, 5 mmol) in 45 ml of acetonitrile was added 5 ml of 1 N-HCl, and the mixture was stirred at room temperature for 4 hours. This reaction mixture was concentrated under reduced pressure and extracted with cyclohexane, and the extract was crystallized by concentration. The resulting slurry was filtered and dried in vacuo to give white crystals. This product was identified to be the title compound.

EXAMPLE 5

Process for Producing the Diol Lactone (compound of the formula (3))

To a solution of KOH (7.92 g) in 100 ml of isopropyl alcohol was added 8.09 g (20 mmol) of lovastatin, and the mixture was stirred under argongas at room temperature for 30 minutes. The temperature was raised and the mixture was further stirred at the reflux temperature for 4 hours. This reaction mixture was concentrated under reduced pressure and the residue was added with water, acidified with phosphoric acid (pH=3.5), and extracted with 200 ml of isopropyl acetate. To the extract was added 65 μl (1 mmol) of methanesulfonic acid, and the mixture was concentrated to about ⅕ volume under reduced pressure. The residue was washed with saturated aqueous solution of sodium hydrogencarbonate and caused to crystallize out at −20° C. This was followed by filtration and drying in vacuo to give white crystals. This product was identified to be the title compound.

EXAMPLE 6

Process for Product for Producing Simvastatin (compound of the formula (6))

To a solution of white crystals of the diol lactone (5 mmol) obtained in Example 5 in 25 ml of methylene chloride were added 3.69 ml (30 mmol) of 2,2-dimethoxypropane and 48 mg (0.25 mmol) of p-toluenesulfonic acid, and the mixture was stirred under argon gas at room temperature for 1 hour. This reaction mixture was added with pyridine and concentrated under reduced pressure.

To a solution of the residue obtained above in 16.2 ml (40 mmol) of pyridine were added 122 mg (1 mmol) of 4-dimethylaminopyridine and 2.69 g (20 mmol) of 2,2-dimethylbutyryl chloride, and the mixture was stirred at 100° C. for 6 hours. This reaction mixture was concentrated under reduced pressure and the residue was added with ethyl acetate. The organic layer was washed with 10% aqueous solution of citric acid and concentrated under reduced pressure.

To a solution of the residue thus obtained in 45 ml of acetonitrile was added 5 ml of 1 N-HCl, and the mixture was stirred at room temperature for 4 hours. This reaction mixture was concentrated under reduced pressure and extracted with cyclohexane and the extract was crystallized by concentration. The resulting slurry was filtered and dried in vacuo to give white crystals. This product was identified to be the title compound.

EXAMPLE 7

Process for Producing 2,2-dimethyl-6(R)-(2-(8(S)-hydroxy-2(S),6(R)-dimethyl-1,2,6,7,8,8a(R)-hexahydronaphthyl-1(S))ethyl)-4(R)-(methyloxycarbonyl)methyl-1,3-dioxane (compound of the formula (4))

Using 2-propanol in lieu of the deacylation reaction solvent used in Example (1), 8.09 g (20 mmol) of lovastatin was deacylated under otherwise the same conditions as in Example (1) and acidified with phosphoric acid to prepare an aqueous solution. The product triol acid in the solution was extracted using toluene as the extraction solvent. This toluene extract (305 g) was concentrated under reduced pressure to about ⅓ so as to remove the concomitant water. Then, 190 mg (1 mmol) of p-toluenesulfonic acid was added, after which 12.5 g (120 mmol) of 2,2-dimethoxypropane was further added. The resulting mixture was stirred under nitrogen gas at room temperature for 1 hour. One hour after the start of reaction, the reaction mixture was sampled and analyzed by HPLC to confirm that the objective triol acid derivative (compound of the formula (4)) had formed in a yield of not less than 90%. This reaction mixture was neutralized with pyridine, added with water, and stirred to extract the p-toluenesulfonic acid pyridinium salt, the byproduct methanol and acetone into the aqueous phase. The toluene solution separated was concentrated under reduced pressure to remove the concomitant water and residual dimethoxypropane to give a toluene solution (80.1 g) of the objective triol acid derivative (compound of the formula (4)).

EXAMPLE 8

Process for Producing 2r2-dimethel-6(R)-(2-(8(S)-(2,2-dimethylbutyryloxy)-2(S),6(R)-dimethyl-1,2,6,7,8,8a(R)-hexahydronaphthyl-1(S))ethyl)-4(R)-(methyloxycarbonyl)methyl-1,3-dioxane (compound of the formula (5))

To a toluene solution (40.0 g) of the triol acid derivative (compound (4)) obtained in Example 7 were added 15.8 g (200 mmol) of pyridine, 122 mg (1 mmol) of 4-dimethylaminopyridine and 5.38 g (40 mmol) of 2,2-dimethylbutyryl chloride, and the mixture was stirred under nitrogen at 100° C. for 6 hours. Six hours after the start of reaction, a portion of the reaction mixture was quantitated by HPLC analysis to confirm that the objective simvastatin derivative (compound (5)) had formed at a conversion rate of not less than 70%. After 8 hours of reaction, the reaction mixture was added with water and stirred at room temperature for 3 hours to decompose the residual acid chloride to the carboxylic acid. The aqueous solution was separated to remove the water-soluble impurity inclusive of the carboxylic acid and pyridine. The organic solution was f urther washed with water 3 times to give 42 g of a toluene solution of the objective compound (compound (5)) with a residual pyridine content of not more than 1%.

EXAMPLE 9

Process for Producing Simvastatin (compound of the formula (6))

To 20 g of the toluene solution of simvastatin derivative (compound (5)) obtained in Example 8 was added 20 ml of 1 N-HCl, and the mixture was stirred vigorously under nitrogen gas at room temperature. After 10 hours, it was confirmed by TLC that the starting simvastatin derivative (compound (5)) had disappeared substantially completely, and after addition of 200 ml of toluene, the aqueous layer was separated. The organic layer was washed with water and further with saturated aqueous solution of sodium chloride. Then, 38 mg (0.2 mmol) of p-toluenesulfonic acid was added and the lactonization reaction was started by heating and refluxing under nitrogen. After 6 hours, a portion of the reaction mixture was taken and analyzed by HPLC. The result indicated that the objective simvastatin had been obtained in a conversion rate of not less than 95%. After cooling, the reaction mixture was added and washed with water under stirring and the toluene was concentrated until crystals of simvastatin had separated out. At the time when crystallization was noticed, the system was cooled to 5° C. and the slurry-like solid matter was separated by suction filtration, washed with toluene and dried in vacuo at 50° C. Analysis of the dried product by HPLC revealed formation of simvastatin of 93% purity.

INDUSTRIAL APPLICABILITY

In accordance with the production technology of the present invention, simvastatin of great use as an HMG-CoA reductase inhibitor can be produced from lovastatin with high efficiency.

What is claimed is:
1. A process for producing a diol lactone of the formula (3);

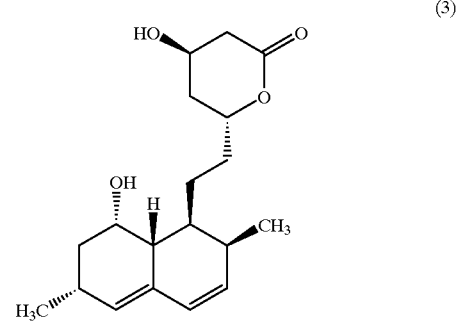

which comprises treating lovastatin of the formula (1) with an inorganic base and a secondary or tertiary alcohol at not more than 100° C. to give a triol acid of the formula (2);

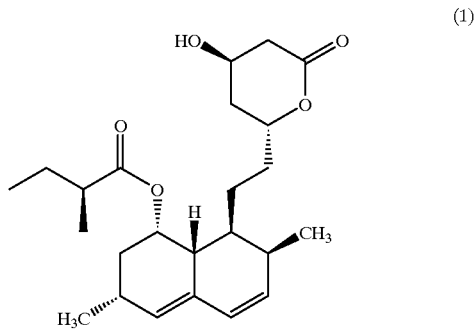

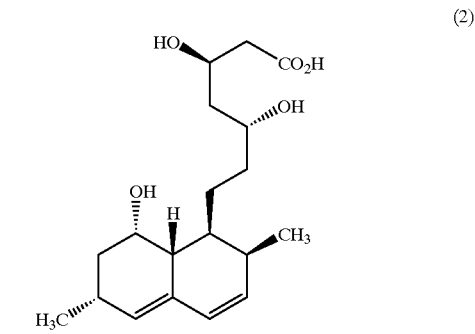

and serially acidifying and lactonizing the triol acid (2) to give a diol lactone (3).
2. The process for producing a diol lactone of the formula (3) according to claim 1
wherein the secondary or tertiary alcohol is i-propanol or t-butanol.

3. The process for producing a diol lactone of the formula (3) according to claim 1
   wherein the inorganic base is an alkali metal hydroxide or an alkali metal alkoxide.
4. The process for producing a diol lactone of the formula (3) according to claim 3
   wherein the alkali metal hydroxide is lithium hydroxide, sodium hydroxide or potassium hydroxide.
5. A process for producing a triol acid derivative of the formula (4);

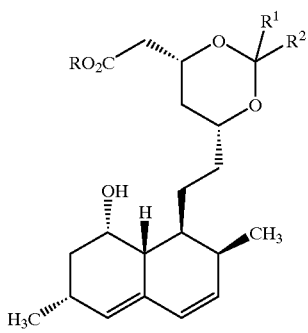
(4)

wherein R represents a lower alkyl group of 1 to 8 carbon atoms; $R^1$ and $R^2$ may be the same or different and each represents hydrogen, a lower alkyl group of 1 to 8 carbon atoms, or an aryl or aralkyl group which may have a substituted group; or $R^1$ and $R^2$ may be coupled together at free ends to form a ring,
which comprises treating a triol acid of the formula (2) or a diol lactone of the formula (3) with an acid and a compound of the formula $(RO)_2CR^1R^2$;
wherein R, $R^1$ and $R^2$ are respectively as defined above, to give a triol acid (4)

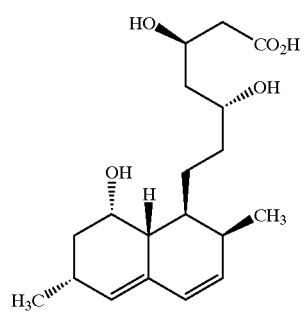
(2)

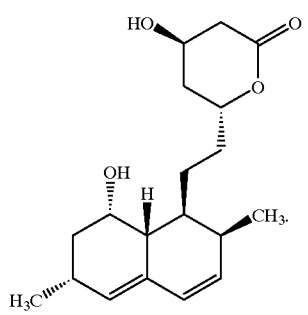
(3)

6. A process for producing a simvastatin derivative of the formula (5);

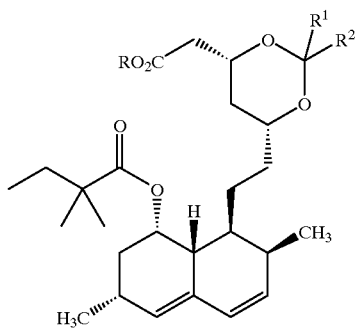
(5)

wherein R represents a lower alkyl group of 1 to 8 carbon atom; $R^1$ and $R^2$ may be the same or different and each represents hydrogen, a lower alkyl group of 1 to 8 carbon atoms, or an aryl or aralkyl group which may have a substituted group; or $R^1$ and $R^2$ may be coupled together at free ends to form a ring,
which comprises treating a triol acid derivative (4) with 2,2-dimethylbutyryl chloride to give a simvastatin derivative (5);

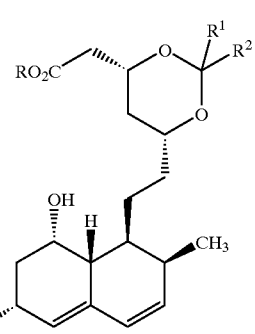
(4)

wherein R, $R^1$ and $R^2$ are respectively as defined above.

7. A process for producing a simvastatin of the formula (6);

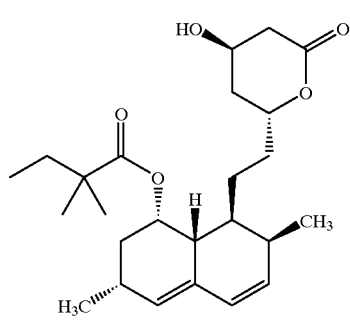
(6)

which comprising treating a simvastatin derivative of the formula (5) with a protic solvent and an acid to give simvastatin (6);

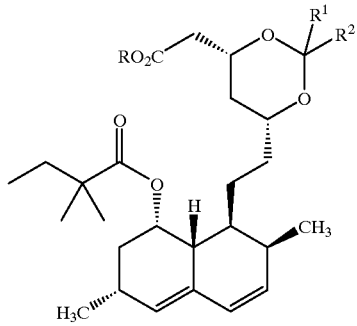
(5)

wherein R represents a lower alkyl group of 1 to 8 carbon atom; $R^1$ and $R^2$ may be the same or different and each represents hydrogen, a lower alkyl group of 1 to 8 carbon atoms, or an aryl or aralkyl group which may have a substituted group; or $R^1$ and $R^2$ may be coupled together at free ends to form a ring.

8. A process for producing a simvastatin of the formula (6);

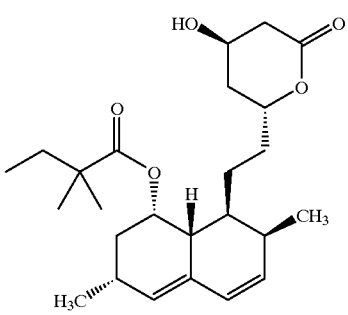
(6)

which comprises treating lovastatin of the formula (1) with an inorganic base and a secondary or tertiary alcohol to give a triol acid of the formula (2);

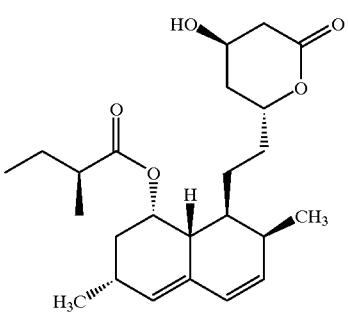
(1)

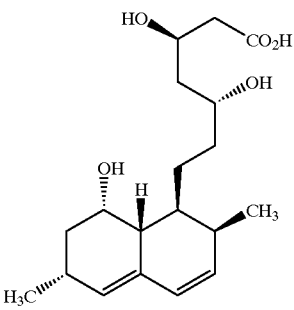
(2)

serially acidifying and lactonizing the triol acid (2) to give a diol lactone of the formula (3);

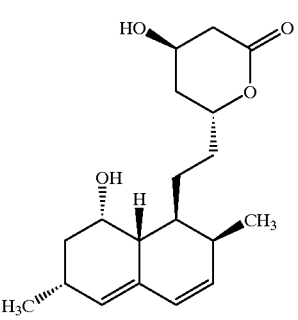
(3)

treating the diol lactone (3) with an acid and a compound of the formula $(RO)_2CR^1R^2$;
  wherein R represents a lower alkyl group of 1 to 8 carbon atoms;
  $R^1$ and $R^2$ may be the same or different and each represents hydrogen, a lower alkyl group of 1 to 8 carbon atoms, or an aryl or aralkyl group which may have a substituted group; or $R^1$ and $R^2$ may be coupled together at free ends to form a ring, to give a triol acid derivative of the formula (4);

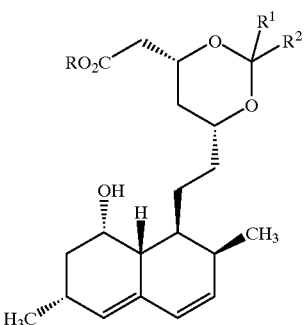
(4)

wherein R, $R^1$ and $R^2$ are respectively as defined above,
treating the triol acid derivative (4) with 2,2-dimethylbutyryl chloride to give a simvastatin derivative of the formula (5);

(5)

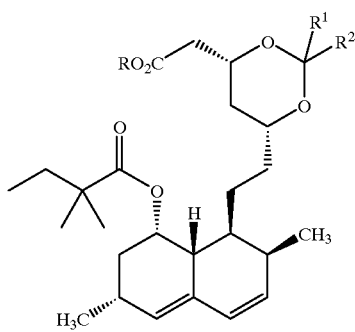

wherein R, R¹ and R² are respectively as defined above, and treating the simvastatin derivative (5) with a protic solvent and an acid to give a simvastatin (6).

9. The process according to claim 5 wherein R=R¹=R²= methyl.

10. A triol acid derivative of the formula (4);

(4)

wherein R, R¹ and R² each represents methyl group.

11. A simvastatin derivative of the formula (5);

(5)

wherein R, R¹ and R² each represents methyl group.

12. The process for producing a diol lactone of the formula (3) according to claim 2 wherein the inorganic base is an alkali metal hydroxide or an alkali metal alkoxide.

13. The process according to claim 6 wherein R=R¹=R²= methyl.

14. The process according to claim 7 wherein R=R¹=R²= methyl.

15. The process according to claim 8 wherein R=R¹=R²= methyl.

16. The process for producing a diol lactone of the formula (3) according to claim 1, wherein the reaction temperature for treating lovastatin of the formula (1) is 60 to 100° C.

17. The process for producing a diol lactone of the formula (3) according to claim 1, wherein the reaction time for treating lovastatin of the formula (1) with an inorganic base and a secondary or tertiary alcohol is 1 to 60 hours.

\* \* \* \* \*